United States Patent [19]

Sommer et al.

[11] 4,308,147

[45] Dec. 29, 1981

[54] COMPOSITION AND TREATING AQUEOUS SOLUTIONS WITH N-CARBOXY ALKYL AMINO ALKANE POLYPHOSPHONIC ACIDS AND THEIR ALKALI METAL SALTS

[75] Inventors: Klaus Sommer, Heidelberg; Hermann Weber, Hemsbach, both of Fed. Rep. of Germany

[73] Assignee: Benckiser-Knapsack GmbH, Ladenburg Am Neckar, Fed. Rep. of Germany

[21] Appl. No.: 91,895

[22] Filed: Nov. 7, 1979

Related U.S. Application Data

[62] Division of Ser. No. 926,301, Jul. 20, 1978.

[30] Foreign Application Priority Data

Jul. 20, 1977 [DE] Fed. Rep. of Germany ....... 2732777

[51] Int. Cl.³ .................................................. C02F 5/14
[52] U.S. Cl. .................................... 210/700; 252/180; 260/502.5
[58] Field of Search ................ 210/54, 58, 698–700; 252/180, 181; 260/502.5, 534 R

[56] References Cited

U.S. PATENT DOCUMENTS

| | | | |
|---|---|---|---|
| 2,609,390 | 9/1952 | Bersworth | 260/502.5 |
| 3,288,846 | 11/1966 | Irani et al. | 260/502.5 |
| 3,455,675 | 7/1969 | Irani | 260/502.5 |
| 3,907,652 | 9/1975 | Wagenknecht | 260/502.5 |
| 3,914,162 | 10/1975 | Kowalski | 260/502.5 |
| 3,992,294 | 11/1976 | Scharf et al. | 210/58 |
| 4,029,696 | 7/1977 | Sommer et al. | 210/58 |
| 4,033,896 | 7/1977 | Mitchell et al. | 260/502.5 |
| 4,079,006 | 3/1978 | Mitchell | 210/58 |

FOREIGN PATENT DOCUMENTS

2318416  11/1974  Fed. Rep. of Germany .

Primary Examiner—Peter A. Hruskoci
Attorney, Agent, or Firm—Schwartz, Jeffery, Schwaab, Mack, Blumenthal & Koch

[57] ABSTRACT

Disclosed are a composition and method for treating aqueous solutions with N-carboxy alkyl amino alkane polyphosphonic acids which have more than two carbon atoms in their carboxy alkyl group, and their alkali metal salts. The acids and salts are prepared in a good yield by reacting alkali metal salts of amino alkane phosphonic acids in which at least one hydrogen atom of the amino group is unsubstituted, in an alkaline medium with an $\alpha,\beta$-unsaturated carboxylic acid at increased temperature. The free acids are preferably recovered from the reaction solution by a treatment with a cation exchange agent. In place of the $\alpha,\beta$-unsaturated carboxylic acids there can also be used their anhydrides, esters, or nitriles. The resulting polyphosphonic acids have a good complexing or sequestering effect on polyvalent metal ions.

6 Claims, No Drawings

COMPOSITION AND TREATING AQUEOUS SOLUTIONS WITH N-CARBOXY ALKYL AMINO ALKANE POLYPHOSPHONIC ACIDS AND THEIR ALKALI METAL SALTS

This is a division, of application Ser. No. 926,301, filed July 20, 1978.

BACKGROUND OF THE INVENTION (1) Field of the Invention

The present invention relates to novel and highly advantageous N-carboxy alkyl amino alkane polyphosphonic acids and their alkali metal salts and more particularly to such polyphosphonic acids which have more than two carbon atoms in their carboxy alkyl group, to a process of producing such compounds, and to compositions for and a method of using the same.

(2) Description of the Prior Art

In German Pat. No. 23 18 416 there are described N-carboxy methyl amino alkane or aryl alkane diphosphonic acids. Such acids are produced by reacting amino alkane or aryl alkane diphosphonic acids in an alkaline medium with formaldehyde and an alkali metal cyanide at a temperature between about 70° C. and about 150° C. By cyano alkylation there are obtained the corresponding cyano methyl aminoalkane or aryl alkane diphosphonic acids.

Subsequently the nitrile group of the resulting compounds is saponified to the carboxyl group.

The phosphonic acids described in said patent are characterized by a high water solubility, by a satisfactory complexing and sequestering power with respect to polyvalent metal ions and when used even in sub-stoichiometric amounts, by an especially high stabilizing power with respect to the hardness-forming compounds present in water.

The disadvantages of the process of producing such compounds according to said German Patent No. 23 18 416 are that only carboxy methyl amino alkane or aryl alkane phosphonic acids can be produced in a satisfactory manner and that working with alkali metal cyanides requires extensive precautionary measures in carrying out this process. Higher molecular carboxy alkyl compounds could not be prepared in a satisfactory yield by using higher aldehydes in place of formaldehyde.

SUMMARY OF THE INVENTION

It is an object of the present invention to provide a method of using N-carboxy alkyl amino alkane polyphosphonic acids or their alkali metal salts as complexing and sequestering agents with respect to polyvalent metal ions, as agents for preventing scale and deposit formation in aqueous media, and for other purposes.

Another object of the present invention is to provide valuable and highly effective compositions containing such compounds as complexing or sequestering agents with respect to polyvalent metal ions, for preventing or reducing scale and deposit formation in aqueous media even in substoichiometric amounts, and for other purposes.

Other objects of the present invention and advantageous features thereof will become apparent as the description proceeds.

The compositions according to the invention contain N-carboxy alkyl amino alkane polyphosphonic acids which have more than two carbon atoms in their carboxy alkyl group correspond to the following formula 1:

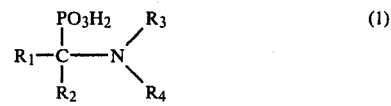

in which
$R_1$ is hydrogen, lower alkyl and especially methyl or ethyl, lower hydroxy alkyl and especially hydroxy ethyl, lower carboxy alkyl and especially carboxy methyl, aryl and especially phenyl, a lower alkyl phosphonic acid group of the formula $—C_nH_{2n}PO_3H_2$ and preferably the lower alkyl phosphonic acid group in which n indicates the numerals 1 or 2, or the group of the formula

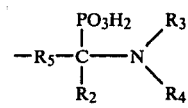

$R_5$ in said formula being lower alkylene;
$R_2$ is hydrogen or the phosphonic acid group $PO_3H_2$;
$R_3$ is hydrogen, lower alkyl and especially methyl or ethyl, or a lower alkyl phosphonic acid group and especially the methyl phosphonic acid group of the formula $—CH_2PO_3H_2$ with the proviso that, when $R_3$ is the methyl phosphonic acid group, then $R_1$ and $R_2$ are hydrogen; and $R_4$ is a carboxy lower alkyl group of the formula $—(CH_2)_m—COOH$ in which m is preferably one of the numerals 2 to 5, or a group of the formula

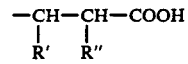

in which
$R'$ is hydrogen, lower alkyl and especially methyl, carboxy lower alkyl and especially carboxy methyl, or carboxyl; and
$R''$ is hydrogen, lower alkyl and especially methyl, or carboxy lower alkyl and especially carboxy methyl.

DESCRIPTION OF PREFERRED EMBODIMENTS

The novel N-carboxy alkyl amino alkane polyphosphonic acids with more than two carbon atoms in their carboxy alkyl group are produced in a highly advantageous manner from alkali metal salts of amino alkane phosphonic acids with at least one unsubstituted hydrogen atom at the amino group. Such starting materials correspond to the following formula 2:

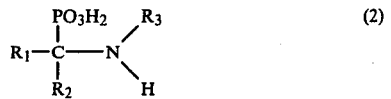

in which
$R_1$ is hydrogen, lower alkyl and especially methyl and ethyl, hydroxy lower alkyl and especially hydroxy ethyl, carboxy lower alkyl and especially carboxy methyl, aryl and especially phenyl, a lower alkyl phosphonic acid group of the formula $—C_nH_{2n}PO_3H_2$ and preferably a lower alkyl phosphonic acid group in which n indicates the numerals 1 or 2 or a group of the formula

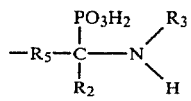

$R_5$ in said formula being lower alkylene;

$R_2$ is hydrogen or the phosphonic acid group $-PO_3H_2$; and $R_3$ is hydrogen, lower alkyl and especially methyl or ethyl, or a lower alkyl phosphonic acid group and especially the methyl phosphonic acid group of the formula $-CH_2PO_3H_2$; with the proviso that, when $R_3$ is the methyl phosphonic acid group, then $R_1$ and $R_2$ are hydrogen.

Said starting materials are reacted with alkali metal salts of unsaturated carboxylic acids of the formula 3:

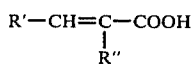

in which

R' is hydrogen, lower alkyl and especially methyl, carboxy lower alkyl and especially carboxy methyl, or the carboxyl group; and R" is hydrogen, lower alkyl, and especially methyl, or carboxy lower alkyl and especially carboxy methyl. The reaction takes place in an aqueous medium and at an increased temperature. Preferably the free carboxylic acids are set free from the reaction mixture by means of ion exchange agents.

Suitable amino alkane phosphonic acid starting materials are the following:
Amino methane diphosphonic acids;
1-amino ethane-1,1-diphosphonic acid;
1-amino propane-1,1-diphosphonic acid;
3-hydroxy-1-amino propane-1,1-diphosphonic acid;
1-hydroxy-3-amino propane-1,1-diphosphonic acid;
2-carboxy-1-amino ethane-1,1-diphosphonic acid;
phenyl amino methane diphosphonic acid;
1-amino propane-1,1,3-triphosphonic acid;
imino-bis-methane phosphonic acid;
1,6-diamino hexane-1,1,6,6-tetraphosphonic acid;
and the like.

Preferably the following unsaturated carboxylic acids are used as the other reactants.
Acrylic acid;
methacrylic acid;
crotonic acid;
maleic acid;
fumaric acid;
itaconic acid;
citraconic acid;
and the like acids.
Amino alkane monophosphonic acids, for instance, amino methane phosphonic acid;
1-amino ethane-2-phosphonic acid;
1-amino propane-3-phosphonic acid,
or the like can, of course, also be used in said reaction. The carboxy alkyl derivatives obtained thereby, however, have a lower complex forming power than the corresponding polyphosphonic acids.

The reaction according to the present invention is carried out in such a manner that solutions of the alkali metal salts of the amino alkane phosphonic acids are reacted with the alkali metal salts of the $\alpha,\beta$-unsaturated carboxylic acids at increased temperature, especially at a temperature between about 50° C. and about 180° C. and preferably between about 60° C. and about 140° C. It is also possible to proceed in such a manner that the phosphonic acids are first dissolved with the $\alpha,\beta$-unsaturated carboxylic acids in an alkali metal hydroxide solution whereafter the resulting reaction solution is reacted at the abovegiven temperatures.

Furthermore, the reaction may be effected by charging the reaction vessel with an aqueous alkali metal hydroxide solution and by gradually introducing thereinto the phosphonic acid and the unsaturated carboxylic acid while stirring. Subsequently the reaction mixture is heated for some time to complete the reaction.

In some instances it can be of advantage to use, in place of the acids or their alkali metal salts, the nitriles or esters of the respective carboxylic acids. Thus, for instance, the reaction may be carried out by using unsaturated nitriles such as acrylonitrile, methacrylonitrile, and the like nitriles as starting materials. In this case, of course, a saponification step is required subsequently to the main reaction process.

In place of the $\alpha,\beta$-unsaturated acids, there can also be used their anhydrides as reactants.

Although the alkali metal salts of the starting amino alkane phosphonic acids are the preferred salts, there can also be used their salts with tertiary amines such as trimethylamine or triethanolamine.

When proceeding in the above-described manner, the alkali metal salts of the N-carboxy alkyl amino alkane polyphosphonic acids of the above given formula 1 are obtained.

According to the process of the present invention there are obtained, for instance, the following compounds:
N-(2-carboxy ethyl) amino methane diphosphonic acid;
N-(2-carboxy ethyl)-1-amino ethane-1,1-diphosphonic acid;
N-methy-N-(2-carboxy ethyl) amino methane diphosphonic acid;
N-ethyl-N-(2-carboxy ethyl) amino methane diphosphonic acid;
N-(2-methyl-2-carboxy ethyl) amino methane diphosphonic acid;
N-(2-methyl-2-carboxy ethyl)-1-amino ethane-1,1-diphosphonic acid;
N-(1-methyl-2-carboxy ethyl) amino methane diphosphonic acid;
N-(1-methyl-2-carboxy ethyl)-1-amino ethane-1,1-diphosphonic acid;
N-(1,2-dicarboxy ethyl) amino methane diphosphonic acid;
N-(1,2-dicarboxy ethyl)-1-amino ethane-1,1-diphosphonic acid;
N-(2,3-dicarboxy propyl) amino methane diphosphonic acid;
N-(2,3-dicarboxy propyl)-1-amino ethane-1,1-diphosphonic acid;
N-(1,2-dicarboxy propyl) amino methane diphosphonic acid;
N-(1,2-dicarboxy propyl)-1-amino ethane-1,1-diphosphonic acid;
N,N-bis-phosphono methyl-3-amino propionic acid;
N,N-bis-phosphono methyl-3-amino succinic acid;

N,N-bis-phosphone methyl-2-amino methyl succinic acid;
N,N-bis-phosphono methyl-1-methyl-2-amino succinic acid,
and others.

The N-carboxy alkyl amino alkane polyphosphonic acids and their alkali metal salts as they are obtained according to the present invention possess at least the same advantageous properties as the compounds described in German Pat. No. 23 18 416. The acids as well as the alkali metal salts can be employed in all those instances in which a good complexing or sequestering action with respect to polyvalent metal ions is required. Thus, they can be employed for the treatment of water and for water softening, for the treatment and the improvement of the properties of textile materials, in the production of cellulose and paper, and in other instances in which the negative effect of polyvalent cations is to be reduced or eliminated. The new polyphosphonic acids are distinguished, for instance, over heretofore used polyphosphates by their stability against hydrolysis at temperatures exceeding 100° C. They also prevent, or considerably reduce, when employed in substoichiometric amounts, scale and deposit formation caused by water hardness-forming agents. Furthermore, they can also be used as additives to photographic and electroplating or galvanizing baths. They have proved of value in retarding setting or gypsum or cement.

It is a noteworthy advantage of the process according to the present invention that, in addition to the low toxicity of the starting materials, no by-products, which can only be removed and separated with difficulty, are formed during the reaction.

Another advantage of the process of the present invention in addition to the low toxicity of the starting materials consists in the feature that the hydrolysis step can be omitted when using the alkali metal salts of the unsaturated carboxylic acids.

The following examples serve to illustrate the present invention without, however, limiting the same thereto.

EXAMPLE 1

47.8 g. of aminomethane diphosphonic acid and 50 g. of sodium hydroxide are dissolved in 200 cc. of water. 19 g. Of acrylic acid dissolved in 50 cc. of water are added drop by drop thereto at a temperature between 20° C. and 40° C. while stirring vigorously. After the acrylic acid solution has been added, the reaction mixture is kept at a temperature of 90° C. for 30 minutes and is then neutralized with dilute hydrochloric acid. The neutralized solution is passed through a cation exchange agent and the resulting solution is concentrated by evaporation. After allowing the concentrated solution to stand for several days, N-(2-carboxy ethyl) amino methane diphosphonic acid is obtained in the form of crystals.

Yield: 78%.

Analysis of the crystals: Found: 18.9% C; 5.1% N; 23.2% P. Calculated: 18.26% C; 5.32% N; 23.55% P.

Minor amounts of N,N-bis-(2-carboxy ethyl) amino methane diphosphonic acid are formed in some experiments. Said diphosphonic acid can be demonstrated by thin layer chromatogram and can also be isolated and analyzed.

The N-(2-carboxyl ethyl) amino methane diphosphonic acid obtained as described hereinabove exhibits a calcium oxide binding power of 34.2 g. Ca/100 g. of acid at a pH of 10.0 as determined by means of the oxalate method. The oxalate method is carried out as follows:

1 g. of the phosphonate to be tested is dissolved in distilled water and made up to 100 cc. of aqueous solution. 25 cc. of said solution are transferred by means of a pipette into a 400 cc. glass beaker. 100 cc. of distilled water and 1 cc. of a saturated ammonium oxalate solution are added thereto. A calcium chloride solution containing 3.96 g. of calcium chloride in 1000 cc. of distilled water is added drop by drop to the mixture of the solutions while continuously stirring until the turbidity does not disappear but remains. Any excess of calcium ions forms with the oxalate ions insoluble calcium oxalate causing the turbidity. The end point of the titration can be recognized quite easily when placing the glass beaker upon a black base and placing water in the space between the bottom of the glass beaker and base.

Calculation:
$$\frac{\text{cc. of solution times ``German hardness'' times 40}}{56 \text{ times } 2.50} = \text{g.Ca/1g. of phosphonic acid.}$$

When using in example 1, in place of amino methane diphosphonic acid, 51.3 g. of N-methylamino methane diphosphonic acid and otherwise proceeding as described therein, N-methyl-N-carboxy ethyl amino methane diphosphonic acid is obtained.

Likewise, N-ethylamino methane diphosphonic acid yields the corresponding N-ethyl-N-carboxy ethyl amino methane diphosphonic acid.

EXAMPLE 2

95.5 g. Of amino methane diphosphonic acid and 100 g. of sodium hydroxide are dissolved in 400 cc. of water. A solution of 50 g. of maleic acid anhydride in 100 cc. of ethanol is added drop by drop thereto while stirring vigorously. After addition is completed, stirring of the reaction solution is continued at room temperature for one hour. The solution is then heated under reflux for six hours. After evaporating the alcohol in a water-jet vacuum, the solution is slightly acidified with dilute hydrochloric acid so as to precipitate non-reacted amino methane diphosphonic acid a kryptocrystalline precipitate which is removed by filtration. The resulting filtrate is treated with a cation exchange agent in order to recover the free N-(1,2-dicarboxy ethyl) amino methane diphosphonic acid. Said phosphonic acid has a calcium oxide binding power of 28.6 g. Ca/100 g. of acid at a pH of 10.0 as determined by means of the oxalate method.

Yield: 73%.

EXAMPLE 3

47.8 g. of amino methane diphosphonic acid or 51.5 g. of amino ethane diphosphonic acid and 84 g. of potassium hydroxide are dissolved in 200 cc. of water. A solution of 23 g. of maleic acid in 60 cc. of water is added drop by drop thereto at a temperature of 25° C. to 40° C. while stirring. The reaction mixture is then heated under reflux for four hours and is treated with a cation exchange agent. The resulting acid solution is concentrated by evaporation in a water-jet vacuum.

Yield: 70%.

Analysis of the N-(1,2-dicarboxy ethyl) amino methane diphosphonic acid obtained thereby:
Found: 19.1% C; 4.8% N; 20.4% P; Calculated: 19.56% C; 4.56% N; 20.17% P.

The N-(1,2-dicarboxy ethyl)-1-amino ethane-1,1-diphosphonic acid obtained in the same manner from amino ethane diphosphonic acid showed the following analytical values:
Found: 23.0% C; 4.5% N; 19.8% P. Calculated: 23.44% C; 4.36% N; 19.29% P.

EXAMPLE 4

102.5 g. of amino ethane diphosphonic acid and 112 g. of potassium hydroxide are dissolved in 500 cc. of water while heating. The solution is allowed to cool to room temperature and a solution of 28 g. of acrylonitrile in 25 cc. of ethanol is added slowly drop by drop thereto while stirring. After addition of the acrylonitrile is completed, the temperature of the reaction mixture is increased to 50° C. The mixture is kept at said temperature for 20 minutes to 30 minutes, whereafter the temperature is further increased to the boiling point of the solution. The reaction solution is boiled for two hours whereby care must be taken that the pH of the solution during hydrolysis is maintained above 8.0. After treating the reaction solution with a cation exchange agent, the resulting crystalline product is obtained in a yield of 79%. It shows the following analytical values:
Found: 21.0% C; 5.1% N; 22.9% P; Calculated: 21.67% C; 5.32% N; 22.44% P.

EXAMPLE 5

54.8 g. of 1-amino propane-1,1-diphosphonic acid and 40 g. of sodium hydroxide are dissolved in 150 cc. of water. 10 g. of sodium hydroxide dissolved in 40 cc. of water and 22 g. of crotonic acid dissolved in 50 cc. of water are added drop by drop simultaneously thereto while stirring vigorously. After continuing stirring for one hour, the temperature of the reaction mixture is increased to 100° C. and the reaction solution is boiled under reflux for 3 hours. It is then slightly acidified with hydrochloric acid. Any turbidity occurring thereby is removed by filtration. After treating the solution with an acid ion exchange agent, the N-(1-carboxy propyl)-1-amino propane-1,1-diphosphonic acid is obtained as an oily residue. This residue is mixed with 100 cc. of ethanol, the ethanol is decanted, and the residue is dried.
Analysis: Found: 28.0% C; 4.8% N; 20.4% P; Calculated: 27.55% C; 4.59% N; 20.30% P.

EXAMPLE 6

66.8 g. of phenyl amino methane diphosphonic acid and 70 g. of potassium hydroxide are dissolved in 250 cc. of water. 19 g. of acrylic acid or 23 g. of methacrylic acid, dissolved in 60 cc. of water, are added drop by drop thereto while stirring vigorously. Thereafter, the procedure is the same as described in Example 1. The yield of the resulting carboxylated acids is between about 72% and 75%. The analysis of N-(2-carboxy ethyl) phenyl amino methane diphosphonic acid showed the following values:
Found: 35.9% C; 4.0% N; 19.0% P; Calculated: 35.41% C; 4.13% N; 18.26% P;
while the analysis of N-(2-methyl-2-carboxy ethyl) phenyl amino methane diphosphonic acid resulted in the following values:
Found: 37.9% C; 4.1% N; 18.1% P; Calculated: 37.37% C; 3.96% N; 17.55% P.

EXAMPLE 7

The carboxy ethyl derivative of the 1,6-di-amino hexane-1,1,6,6-tetraphosphonic acid is prepared in an analogous manner as described in Example 1 from 59.3 g. of 1,6-di-amino hexane-1,1,6,6 tetraphosphonic acid, 50 g. of sodium hydroxide, and 19 g. of acrylic acid. Yield 66% of the theoretical yield.
Analysis: Found: 24.3% C; 4.7% N; 21.9% P; Calculated: 24.84% C; 4.83% N; 21.35% P.

EXAMPLE 8

A solution of the potassium salt of N,N-bis phosphonomethane-2-amino succinic acid is obtained, by proceeding as described in Example 3, from 51 g. of imino bis-methane phosphonic acid, 84 g. of potassium hydroxide and 25 g. of maleic acid. After treating the solution with a cation exchange agent and evaporating the treated solution to dryness, the oily residue shows the following analytical values:
Found: 4.4% N; 19.8% P; Calculated: 4.36% N; 19.29% P.

Of course, many changes and variations in the reactants to be used, in the reaction conditions, temperature and duration to be employed, in the process of working up the reaction solutions and of isolating the reaction products, and the like may be made by those skilled in the art in accordance with the principles set forth herein and in the claims annexed hereto.

Thus, for instance, for recovering the free polyphosphonic acids from the reaction mixture there may be used any of the known ion exchange agents. Strongly acid cation exchange agents as they are commercially available have proved to be especially useful for this purpose, such as, for instance, sulfonated polymers of styrene or divinyl benzene as they are known under the trademarks "Duolite C 25" of the firm Diamond Alkali Co., "Amberlite IR 112 and IR 120" of the firm Rohm & Haas Co., "Dowex 50" of the firm The Dow Chemical Co., "Lewatite S100" of the firm Farbenfabriken Bayer, and others.

As stated above, the novel N-carboxy alkyl amino alkane polyphosphonic acids of the present invention are valuable complexing and sequestering agents with respect to bivalent or polyvalent metal ions. Thus they can advantageously be employed for preventing scale and deposit formation in aqueous systems, for instance, in textile bleaching baths, in water baths used for sterilizing cans, for preventing formation of resinous deposits in the manufacture of paper, and for other uses for which polyphosphonic acids have been used before.

If desired, the alkali metal, ammonium, or amine salts or the reaction solutions as such without further purification can be used in place of the free acids.

The novel phosphonic acid compounds exert also a high scale inhibiting effect. They can be incorporated into solid or liquid preparations to be added to aqueous media. The new phosphonic acids are also well compatible with the conventional washing and cleansing agents and detergents and can be combined therewith to yield scale formation preventing washing and detergent compositions, such as they are used in automatically operating bottle rinsing machines or for cleaning tanks and the like.

In electroplating baths, for instance, the polyphosphonic acids of the present inventions have proved to be of value for producing bright, well adhering, uniform, and pore-free metal coatings without the addition of the heretofore used toxic metal cyanides. An electroplating bath may be composed, for instance, of
   3% to 4%, by weight, of copper carbonate,
   9% to 10%, by weight, of an alkali metal carbonate,
   10% to 12%, by weight, of a polyphosphonic acid of the present invention, and
   74% to 78% of water.

In photographic baths addition of the polyphosphonic acids of the present invention eliminates the harmful effects of the water hardness-causing agents which are responsible for the formation of spots, stains, and/or fogging of the negatives and prints. Developer solutions are also protected by their presence against decomposition by atmospheric oxygen.

We claim:

1. A composition having a high complexing and sequestering power for polyvalent metal ions and being capable of stabilizing the hardness-causing agents in water, said composition comprising an N-carboxy alkyl amino alkane phosphonic acid of the formula

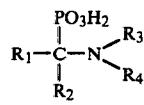

in which
(A)
   $R_1$ is hydrogen;
   $R_2$ is hydrogen;
   $R_3$ is the methylphosphonic acid group; and
   $R_4$ is the group of the formula

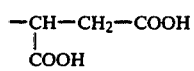

said acid being the N,N-bis-phosphono methane-2-amino succinic acid, or
(B)
   $R_1$ is hydrogen;
   $R_2$ is the phosphonic acid group;
   $R_3$ is hydrogen; and
   $R_4$ is the group of the formula

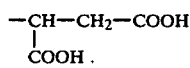

said acid being the N-(1,2-dicarboxy ethyl) amino methane diphosphonic acid, or
(C)
   $R_1$ is methyl;
   $R_2$ is the phosphonic acid group;
   $R_3$ is hydrogen; and
   $R_4$ is the group of the formula

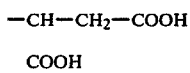

said acid being the N-(1,2-dicarboxy ethyl) amino ethane diphosphonic acid, or
(D)
   $R_1$ is the group

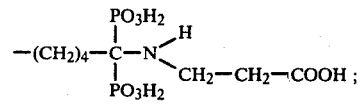

$R_2$ is the phosphonic acid group;
   $R_3$ is hydrogen; and
   $R_4$ is carboxy ethyl;
said acid being the N,N-dicarboxy ethyl-1,6-diamino hexane-1,1,6,6-tetraphosphonic acid; and water.

2. A composition according to claim 1, wherein the N-carboxy alkyl amino alkane polyphosphonic acid has the formula

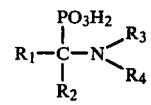

in which
   $R_1$ is hydrogen;
   $R_2$ is hydrogen;
   $R_3$ is the methylphosphonic acid group; and
   $R_4$ is the group of the formula

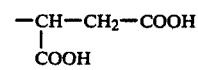

said acid being the N,N-bis-phosphono methane-2-amino succinic acid.

3. A composition according to claim 1, wherein
   $R_1$ is hydrogen;
   $R_2$ is the phosphonic acid group;
   $R_3$ is hydrogen; and
   $R_4$ is the group of the formula

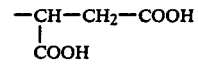

said acid being the N-(1,2-dicarboxy ethyl) amino methane diphosphonic acid.

4. A composition according to claim 1, wherein
   $R_1$ is methyl;
   $R_2$ is the phosphonic acid group;
   $R_3$ is hydrogen; and
   $R_4$ is the group of the formula

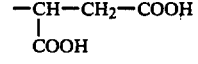

said acid being the N-(1,2-dicarboxy ethyl) amino ethane diphosphonic acid.

5. A composition according to claim 1, wherein
   $R_1$ is the group

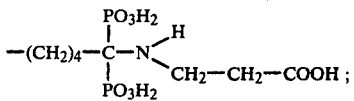

$R_2$ is the phosphonic acid group;
   $R_3$ is hydrogen; and
   $R_4$ is carboxy ethyl;

said acid being the N,N-dicarboxy ethyl-1,6-diamino hexane-1,1,6,6-tetraphosphonic acid.

6. A method of treating an aqueous system for stabilizing polyvalent metal ions, comprising the step of adding to the aqueous system an amount which is sufficient to stabilize the polyvalent metal ions in the system of an N-carboxy alkyl amino alkane phosphonic acid of the formula

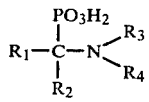

in which
(A)
$R_1$ is hydrogen;
$R_2$ is hydrogen;
$R_3$ is the methylphosphonic acid group; and
$R_4$ is the group of the formula

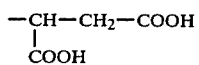

said acid being the N,N-bis-phosphono methane-2-amino succinic acid, or
(B)
$R_1$ is hydrogen;
$R_2$ is the phosphonic acid group;
$R_3$ is hydrogen; and
$R_4$ is the group of the formula

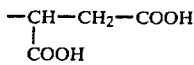

said acid being the N-(1,2-dicarboxy ethyl) amino methane diphosphonic acid, or
(C)
$R_1$ is methyl;
$R_2$ is the phosphonic acid group;
$R_3$ is hydrogen; and
$R_4$ is the group of the formula

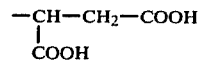

said acid being the N-(1,2-dicarboxy ethyl) amino ethane diphosphonic acid, or
(D)
$R_1$ is the group

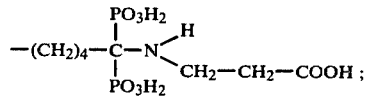

$R_2$ is the phosphonic acid group;
$R_3$ is hydrogen; and
$R_4$ is carboxy ethyl;
said acid being the N,N-dicarboxy ethyl-1,6-diamino hexane-1,1,6,6-tetraphosphonic acid.

* * * * *